United States Patent [19]

Holmes

[11] 4,085,143

[45] Apr. 18, 1978

[54] MANUFACTURE OF $\alpha,\beta$-UNSATURATED ACIDS AND ANHYDRIDES

[75] Inventor: Jerry D. Holmes, Longview, Tex.

[73] Assignee: Eastman Kodak Company, Rochester, N.Y.

[21] Appl. No.: 583,937

[22] Filed: Jun. 5, 1975

[51] Int. Cl.² ...................... C07C 51/00; C07C 51/54
[52] U.S. Cl. .................. 260/515 R; 252/454; 252/455 R; 252/456; 252/457; 252/458; 260/405.5; 260/413; 260/526 N; 260/540; 260/541; 260/546
[58] Field of Search .................. 260/526 N, 546, 413, 260/515 R, 405.5

[56] References Cited

U.S. PATENT DOCUMENTS

| | | | |
|---|---|---|---|
| 3,051,747 | 8/1962 | Leathers et al. | 260/526 N |
| 3,532,740 | 10/1970 | Hargis et al. | 260/526 N |
| 3,840,587 | 10/1974 | Pearson | 260/526 N |
| 3,933,888 | 1/1976 | Schlaefer | 260/526 N |

FOREIGN PATENT DOCUMENTS

| | | | |
|---|---|---|---|
| 847,370 | 10/1939 | France | 260/526 N |
| 1,242,464 | 8/1971 | United Kingdom | 260/526 N |

*Primary Examiner*—Vivian Garner
*Attorney, Agent, or Firm*—Edward R. Weber; Daniel B. Reece, III

[57] ABSTRACT

The present invention relates to a new process for the manufacture of $\alpha,\beta$-unsaturated acids and their anhydrides from formaldehyde, and a saturated acid anhydride containing 1 less carbon atom in the hydrocarbon moiety.

15 Claims, No Drawings

MANUFACTURE OF α,β-UNSATURATED ACIDS AND ANHYDRIDES

The present invention relates to a new process for the manufacture of α,β-unsaturated acids and their anhydrides from formaldehyde and a saturated acid anhydride containing one less carbon in the hydrocarbon moiety, in the vapor phase over a fixed bed catalyst.

α,β-Unsaturated acids and anhydrides are useful as starting materials for various polymers, snythetic resins, and synthetic fibers. The prior art describes the reaction of aromatic aldehydes with anhydrides to give unsaturated acids such as cinnamic acid. These reactions are normally carried out in the liquid phase using basic catalysts. Aliphatic aldehydes such as formaldehyde are unsuitable for this reaction. In the liquid phase, aldehydes normally react with anhydrides to form gem diesters, for example, formaldehyde, when reacted with acetic anhydride, readily gives methylene diacetate (J. F. Walker, "Formaldehyde", 3rd Edition, ACS Monograph Series No. 152, page 350). No prior literature is known which describes the condensation of formaldehyde with an acid anhydride to produce the corresponding α,β-unsaturated acid and/or anhydride.

Therefore, an object of the instant invention is to provide a simplified method for the preparation of an α,β-unsaturated acid or acid anhydride.

It is another object to provide a one-step method for the preparation of an α,β-unsaturated acid or acid anhydride.

A still further object is to provide catalysts useful for promoting the condensation of formaldehyde with a saturated acid anhydride to produce an α,β-unsaturated acid or acid anhydride.

These and other objects, as well as other advantages of this invention will become apparent from a consideration of the specification and claims of this application.

The new process for the manufacture of α,β-unsaturated acids and their anhydrides from formaldehyde and a saturated acid anhydride is believed to proceed in accordance with the following equations:

$$RCH_2-\underset{\underset{O}{\|}}{C}O\underset{\underset{O}{\|}}{C}-CH_2R + CH_2O \longrightarrow CH_2=\underset{\underset{R}{|}}{C}-\underset{\underset{O}{\|}}{C}O\underset{\underset{O}{\|}}{C}-CH_2R + H_2O \quad (1)$$

$$CH_2=\underset{\underset{R}{|}}{C}-\underset{\underset{O}{\|}}{C}O\underset{\underset{O}{\|}}{C}-CH_2R + H_2O \longrightarrow CH_2=\underset{\underset{R}{|}}{C}-\underset{\underset{O}{\|}}{C}OH + RCH_2COOH \quad (2)$$

In the above equations, R can be hydrogen, or an alkyl, aralkyl, or aryl group of from 1–10 carbon atoms, e.g., a straight or branched-chain alkyl group of 1–6 carbon atoms. The alpha carbon must have at least two hydrogens in order to condense with formaldehyde and then eliminate water to first form the partially unsaturated anhydride. The released water can then react with the partially unsaturated anhydride to form the corresponding saturated and unsaturated acids, as shown in equation (2).

In addition, the following interchange reactions occur in the reaction mass during work-up to give a mixture of unreacted saturated anhydride, corresponding saturated acid, α,β-unsaturated anhydride, and the corresponding α,β-unsaturated acid, as shown in the following equations:

$$CH_2=\underset{\underset{R}{|}}{C}-\underset{\underset{O}{\|}}{C}O\underset{\underset{O}{\|}}{C}-CH_2R + CH_2=\underset{\underset{R}{|}}{C}-COOH \rightleftarrows CH_2=\underset{\underset{R}{|}}{C}-\underset{\underset{O}{\|}}{C}O\underset{\underset{O}{\|}}{C}-\underset{\underset{R}{|}}{C}=CH_2 + RCH_2COOH$$

$$CH_2=\underset{\underset{R}{|}}{C}-\underset{\underset{O}{\|}}{C}O\underset{\underset{O}{\|}}{C}-CH_2R + RCH_2COOH \rightleftarrows RCH_2-\underset{\underset{O}{\|}}{C}O\underset{\underset{O}{\|}}{C}-CH_2R + CH_2=\underset{\underset{R}{|}}{C}-COOH$$

The reaction is catalyzed by a broad variety of materials, including sodium carbonate on celatom, sodium carbonate on silica gel, sodium bicarbonate on celatom or silica gel, alkali metal salts of carboxylic acids on inert supports, alkali metal hydroxides on inert supports, alkaline earth hydroxides on inert supports, rare earth oxides on inert supports, silica gel, alumina, silica-alumina, phosphoric acid deposited on alumina or silica gel, boric acid deposited on alumina or silica gel, halophosphoric acids on inert supports, acidic salts such as boron phosphate and aluminum phosphate on inert supports, Lewis acids such as zinc chloride, ferric chloride and stannous chloride on inert supports, the calcined reaction product of the complex obtained when a tin salt is reacted with silica gel at a temperature of from about 60° C. to about 250° C., an oxide of a metal selected from the group Ag, U, Zn, Ti, Zr, Th, Ta, Nb, Mo, W, La, and Sn, supported on an inert support, and a heteropoly acid having the formula $H_a[X^nY_{12}O_m]$ where $X^n$ ($n$ is positive valence) is equal to $P^5$, $As^5$, $Si^4$, $Ge^4$, $Sn^4$, $Ti^4$, $Zr^4$, $Ce^4$, or $Th^4$; Y equals W or Mo; $m$ eqauls 40 or 42; and $a$ equals $8-n$, i.e., $a$ equals 3 when $n$ equals 5 and $a$ equals 4 when $n$ equals 4, which heteropoly acid is supported on an inert support selected from the group consisting of a nondecrepitating silica gel, and a calcined diatomaceous earth.

A preferred catalyst is a metal selected from the group consisting of Ta, Ti, Nb, and Zr, supported upon a relatively low surface area, large pore volume silica gel, such as Davison Chemical Company's G-59. The silica gel supports of the instant invention may have a surface area of less than about 400 square meters per gram and a pore volume greater than about 0.8cc. per gram. For example, the silica gel support may have a surface area of 340 to about 360 square meters per gram and a pore volume of from about 1.00 to about 1.25 cc. per gram.

The catalysts of the instant invention are suitably prepared by conventional methods such as, for example, immersing the support in an aqueous solution of the particular catalytic material selected, and subsequently removing the water by evaporation. Where the desired catalytic material is insoluble, such as an oxide of one of the metals, the oxide may be obtained by calcining a water soluble salt to decompose it into the desired oxide.

The calcining can be carried out at a temperature of from about 400° C. to about 600° C., e.g., from about 500° C. to about 550° C. Moreover, when the catalyst consists of the calcined residue of a mixture of silica gel and a salt or an oxide of a metal selected from the group of tantalum, titanium, niobium and zirconium, the residue can be subsequently heated at a temperature of from about 650° C. to about 1000° C. in the presence of water vapor. For example, the calcined residue can be heated in the presence of water vapor at a temperature of from about 730° C. to about 780° C.

Optimum reaction conditions such as contact time, temperature, amount of diluent gas, feed composition, will vary with the feed material and the particular catalyst selected. In general, the best results are obtained at a contact time of from about 0.1 to about 5 seconds, although this may vary over a much broader range, such as from about 0.1 to about 30 seconds. Particularly good conversions and yields are obtained using a contact time of from about 1 to about 2 seconds.

Preferably the temperature selected will be sufficient to insure vaporization of the reactants and the products. The process may be operated at temperatures of from about 190° C. to about 400° C. Preferred temperature ranges are from about 200° C. to about 300° C.

Super- or subatmospheric pressure may also be utilized to facilitate the reactivity and/or vaporization of the reactants.

Suitable anhydrides include acetic, propionic, phenyl acetic, butyric, pentanoic, and hexanoic.

Formaldehyde may be fed as a gaseous monomer, as trioxane solution, or as a para-formaldehyde slurry. Conversion of the formaldehyde to $\alpha,\beta$-unsaturated acid depends on the type and state of the catalyst and in many cases, the ratio of anhydride to formaldehyde in the feed. Normally, the particular catalyst activity and practical manufacturing considerations will dictate the most desirable ratio of anhydride to formaldehyde fed to the reactor. Good results have been obtained with anhydride to formaldehyde ratios of from about 1.1:1 to about 5:1. The optimum ratio will depend on various manufacturing consideration, such as refining and recycling of unreacted feed materials. There appears to be no upper limit to the molar ratio other than practical manufacturing conditions which arise when a large excess of one material is introduced into a system.

If desired, an inert diluent gas may be utilized to facilitate feeding of the reactants, control of contact time, etc. Good results are obtained at atmospheric pressure, using an inert diluent gas, usually in a molar ratio of gas to organic feed of from about 1:10 to about 20:1, preferably from about 1:1 to about 6:1, and most preferably about 2:1. A suitable inert diluent gas is any gas which does not react with either the reactants or the products under the conditions of the reaction, such as, nitrogen, helium, argon, gaseous hydrocarbons, and compounds which are readily vaporized, such as benzene.

As previously indicated, the reactor effluent contains a mixture of the $\alpha,\beta$-unsaturated acid and acid anhydride in addition to unreacted starting anhydrides, and the corresponding saturated acid formed in the reaction. By distilling out the saturated acid, all the unsaturated acid can be converted to its anhydride by interchange with the excess unreacted starting anhydride. The unsaturated anhydride can then be separated by conventional distillation and can be reacted with water to form the unsaturated acid, or with alcohols to form $\alpha,\beta$-unsaturated esters. Another possibility for work-up is to react the reactor effluent with water to convert all the anhydrides to the corresponding saturated acid and the corresponding saturated and $\alpha,\beta$-unsaturated acids.

The process of the instant invention is illustrated in greater detail by the following examples, which are all conducted at atmospheric pressure, but it will be understood that these examples are not intended to limit the invention in any way, and obvious modifications will occur to those skilled in the art.

EXAMPLE 1

This example illustrates the use of $Ta_2O_5$ on Davison G-59 silica gel as the catalyst for the manufacture of methacrylic acid and anhydride from propionic anhydride and formaldehyde. To a 2 foot by 22 mm. Vycor reactor heated by an electrical furnace is charged 32 milliliters of Vycor chips, then 50 milliliters of a catalyst prepared by depositing tantalum oxalate (5.16 grams as tantalum) on 50 grams of Davison G-59 silica gel, and finally 90 milliliters of Vycor chips which are used to vaporize the feed prior to contacting the catalyst. The catalyst is heated at 550° C. in 2.72 moles per hour of nitrogen for 2 hours and then in air for 1 hour. At this point the catalyst is ready for use and the reactor temperature is set at 215°–240° C. A feed mixture of 685 grams (approximately 98.5 percent purity) propionic anhydride and 90 grams trioxane is prepared and fed to the reactor at a rate of about 60 milliliters per hour. This feed corresponds to a 1.73 to 1 molar ratio of anhydride to formaldehyde. Nitrogen is fed simultaneously with the organic mixture at a rate of 1.25 moles per hour. Over a 5 hour period, 1.2 moles of formaldehyde and 2.08 moles of propionic anhydride are fed through the reactor. A total of 304 grams of product is collected, which by gas liquid chromatographic analysis contains 0.156 mole methacrylic anhydride and 0.56 mole methacrylic acid. This corresponds to a formaldehyde conversion of 73% with a yield of 77% and a propionic anhydride conversion of 42% with a yield of 69 percent.

EXAMPLE 2

This example illustrates the manufacture of acrylic acid and anhydride from acetic anhydride using a $Ta_2O_5$ on silica gel catalyst. The catalyst described in Example 1 is burned clean at 550° C. in air and then all reaction conditions are set essentially the same as used in Example 1. A feed mixture of 714 grams acetic anhydride (approximately 99 percent purity) and 120 grams trioxane is prepared and corresponds to a 1.72 molar ratio of anhydride to formaldehyde. Over a 5 hour period, 1.59 moles of formaldehyde and 2.73 moles of acetic anhydride are fed through the reactor. A total of 319 grams produce is collected, which by gas liquid chromatographic analysis, contains 0.165 mole acrylic anhydride and 0.68 mole acrylic acid. This corresponds to a formaldehyde conversion of 64% with a yield of 70% and an acetic anhydride conversion of 37% with a yield of 64 percent.

EXAMPLE 3

This example illustrates the manufacture of acrylic acid and anhydride from acetic anhydride and formaldehyde using titanium dioxide on silica gel catalyst. This catalyst is prepared by reacting 72 grams titanium tetrachloride in hexane with 100 grams Davision G-59 silica gel at reflux for 5 hours. The catalyst is washed thoroughly with hexane to remove unreacted titanium tetrachloride and is then hydrolyzed with aqueous ammonium hydroxide. Prior to usage, 50 milliliters of the catalyst is heated in the reactor described in Example 1 at 550° C. in 2.72 moles per hour of nitrogen for 2 hours and then in air for approximately 1.5 hour. The temperature is set at 245°–265° C. with nitrogen diluent set at 1.25 moles per hour and the same feed mixture used in Example 2 is fed a 61 milliliters per hour. Over a 3 hour period, formaldehyde conversion to the mixture of acrylic acid and anhydride is 48 percent and the acetic anhydride yield to the same mixture is 52 percent.

EXAMPLE 4

This example illustrates the use of commercial silica-alumina (Davison 970) as a catalyst in our process for manufacturing α,β-unsaturated acids and anhydrides and, in particular, acrylic acid and its anhydride. A 3:1 ratio of anhydride to formaldehyde feed mixture is fed at a rate of approximately 25 milliliters per hour over 50 milliliters of Davison 970 silica-alumina at 245°–260° C. Formaldehyde conversion to the acrylic acid is about 15 percent.

While preferred embodiments of this invention have been described, it is to be understood that widely different modifications of the invention may be made without departing from the spirit and scope of the invention. The invention is not to be limited by the foregoing examples and details of the description, except as defined by the following claims.

I claim:

1. A process for producing an α,β-unsaturated acid anhydride of the type

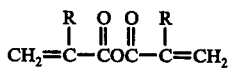

and an α,β-unsaturated acid of the type

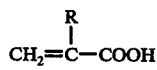

which comprises the steps of reacting an anhydride having the formula

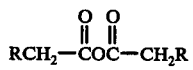

wherein R can be hydrogen or an alkyl, aralkyl, or aryl hydrocarbon moiety of from 1 to 10 carbon atoms with formaldehyde or a formaldehyde yielding material in the vapor phase at a temperature of from about 190° C. to about 400° C. in the presence of an oxide of a metal selected from the group consisting of Ag, U, Zn, Ti, Zr, Th, Ta, Nb, Mo, W, and Sn, supported on an inert support.

2. The process of claim 1 wherein the catalyst is formed by mixing an aqueous solution of a water-soluble salt of a metal selected from the group consisting of Ag, U, Zn, Ti, Zr, Th, Ta, Nb, Mo, W, and Sn, with an inert support, removing the water by evaporation, and subsequently calcining the material at a temperature of from about 400° C. to about 600° C.

3. The process of claim 2 wherein the calcining takes place at a temperature of from about 500° C. to about 550° C.

4. The process of claim 1, wherein the catalyst consists of the calcined residue of a mixture of silica gel and a salt or an oxide of a metal selected from the group consisting of tantalum, titanium, niobium and zirconium which residue has subsequently been heated at a temperature of from about 650° C. to about 1000° C. in the presence of water vapor.

5. The process of claim 4 wherein the catalyst is formed by mixing an aqueous solution of a water soluble salt of the selected heavy metal with silica gel, removing the water by evaporation, calcining the material at a temperature of from about 400° C. to about 600° C. and subsequently heating the calcined residue at elevated temperature in the presence of water vapor.

6. The process according to claim 5 wherein the calcining takes place at a temperature of from about 500° C. to about 550° C.

7. The process according to claim 4 wherein th calcined residue is heated in the presence of water vapor at a temperature of from about 730° C. to about 780° C.

8. The process of claim 7 wherein the calcined residue is heated in the presence of water vapor for a period of from about 3 to about 6 hours.

9. The process of claim 1 wherein R is a straight- or branched-chain alkyl group of 1 to 6 carbon atoms.

10. The process of claim 1 wherein the anhydride is selected from the group consisting of acetic, propionic, phenyl acetic, butyric, pentanoic, and hexanoic anhydrides.

11. The process of claim 1 wherein the support is a silica gel having a surface area of less than about 400 square meters per gram, and a pore volume greater than about 0.8 cc. per gram.

12. The process of claim 11 wherein the support is a silica gel having a surface area of about 340 to about 360 square meters per gram and a pore volume of from about 1.25 cc. per gram.

13. The process according to claim 1 wherein the reaction is conducted at a temperature of from about 200° C. to about 300° C.

14. The process according to claim 1 wherein the reaction is conducted at atmospheric pressure.

15. The process according to claim 1 wherein the ratio of anhydride to aldehyde is from about 1.1:1 to about 5:1.

* * * * *